US010215722B2

(12) United States Patent
Kucera et al.

(10) Patent No.: US 10,215,722 B2
(45) Date of Patent: Feb. 26, 2019

(54) PROVIDING APPLIANCES WITH GAS QUALITY INFORMATION

(71) Applicant: Honeywell International Inc., Morristown, NJ (US)

(72) Inventors: David Kucera, Bilovice nad Svitavou (CZ); Curtis Taylor, Gaston, IN (US)

(73) Assignee: Honeywell International Inc., Morris Plains, NJ (US)

( * ) Notice: Subject to any disclaimer, the term of this patent is extended or adjusted under 35 U.S.C. 154(b) by 792 days.

(21) Appl. No.: 14/300,395

(22) Filed: Jun. 10, 2014

(65) Prior Publication Data

US 2015/0355119 A1 Dec. 10, 2015

(51) Int. Cl.
G01N 25/22 (2006.01)
G01N 30/02 (2006.01)
F23N 1/02 (2006.01)
G01N 33/22 (2006.01)
G01N 30/88 (2006.01)

(52) U.S. Cl.
CPC ............ *G01N 25/22* (2013.01); *F23N 1/022* (2013.01); *G01N 30/02* (2013.01); *G01N 33/225* (2013.01); *F23N 2021/10* (2013.01); *F23N 2039/04* (2013.01); *G01N 2030/8854* (2013.01)

(58) Field of Classification Search
None
See application file for complete search history.

(56) References Cited

U.S. PATENT DOCUMENTS

| 4,749,122 A * | 6/1988 | Shriver | F23N 1/022 |
| | | | 122/448.1 |
| 2013/0139765 A1* | 6/2013 | Huang | F23N 1/082 |
| | | | 122/14.21 |
| 2013/0153798 A1* | 6/2013 | Kucera | F23N 1/002 |
| | | | 251/129.01 |

FOREIGN PATENT DOCUMENTS

| GB | 256523 | * 8/1926 |
| KR | 110022304 | 3/2011 |
| WO | 2011096799 | 8/2011 |
| WO | 2012125022 | 9/2012 |

OTHER PUBLICATIONS

Model CM6G Gas Calorimeter User's Manual, Yokogawa Electric Corporation. http://www.yokogawa.com/an/cm6g/an-cm6g-01en.htm. Accessed on Oct. 29, 2013. 88 pgs.
Flo-Cal™—High Speed Calorimeter, Thermo Scientific. http://www.thermoscientific.com/ecomm/servlet/productsdetail_11152_L10520_80562_11962939_-1. Accessed on Oct. 29, 2013. 6 pgs.

* cited by examiner

Primary Examiner — Daniel S Larkin

(57) ABSTRACT

Methods and systems for providing appliances with gas quality information are described herein. One system includes a single calorimeter or a single gas chromatograph configured to determine a calorific value of a gas being supplied to an area having a plurality of appliances and communicate the calorific value of the gas to the plurality of appliances.

18 Claims, 3 Drawing Sheets

PROVIDING APPLIANCES WITH GAS QUALITY INFORMATION

TECHNICAL FIELD

The present disclosure relates to methods and systems for providing appliances with gas quality information.

BACKGROUND

Appliances used in drying or air heating applications, such as, for instance, paper machines, agricultural grain dryers, tissue machines, and food and beverage (e.g., beer) processing machines, may utilize fuel (e.g., gas) to perform their operations. The air-fuel or oxygen-fuel ratios of such appliances may be controlled to reduce the pollutant emissions of the appliances and/or increase the efficiency of the appliances. However, any change in the quality (e.g., calorific value) of the gas being supplied to the appliances may increase the pollutant emissions of the appliances and/or decrease the efficiency of the appliances, and hence may necessitate an adjustment of the air-fuel or oxygen-fuel ratios of the appliances.

One approach to determining the quality of the gas being supplied to the appliances, and hence whether to adjust the air-fuel or oxygen-fuel ratios of the appliances, can include installing a calorimeter directly upstream of each different appliance (e.g., at the point the gas is input into each appliance). However, calorimeters can be expensive, which can make such an approach cost-prohibitive.

Another approach to determine whether to adjust the air-fuel or oxygen-fuel ratios of the appliances can include installing a gas sensor to measure the composition of the combustion products (e.g., the percent oxygen in the fumes) of the appliances. However, the combustion products of the appliances may be diluted, and therefore may not provide an accurate indication of the quality of the gas being supplied to the appliances.

DETAILED DESCRIPTION

Figure 1:
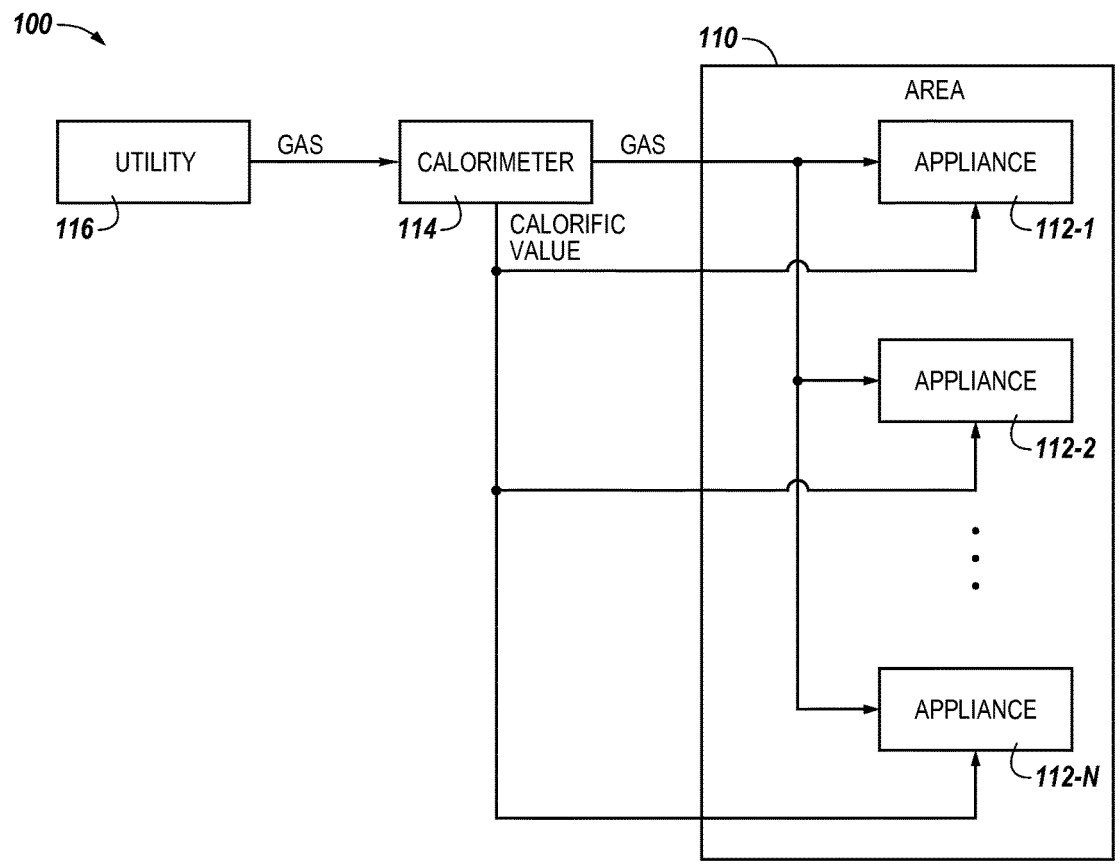
FIG. 1 illustrates an example of a system for providing appliances with gas quality information in accordance with one or more embodiments of the present disclosure.

Methods and systems for providing appliances with gas quality information are described herein. For example, one or more embodiments include a single calorimeter or a single gas chromatograph configured to determine a calorific value of a gas being supplied to an area having a plurality of appliances and communicate the calorific value of the gas to the plurality of appliances.

Embodiments of the present disclosure can utilize a single (e.g., only one) calorimeter to provide different appliances in an area with information about the quality (e.g., the calorific value) of the gas being supplied to the appliances. Accordingly, embodiments of the present disclosure can provide the gas quality information to the appliances at a lower cost than previous approaches (e.g., approaches in which a calorimeter is installed directly upstream of each different appliance). Further, embodiments of the present disclosure can provide more accurate gas quality information to the appliances than previous approaches (e.g., approaches in which gas sensors are installed to measure the composition of the combustion products of the appliances).

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that mechanical, electrical, and/or process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2.

As used herein, "a" or "a number of" something can refer to one or more such things. For example, "a number of light emitting diodes" can refer to one or more light emitting diodes. Further, the designator "N", as used herein, particularly with respect to reference numerals in the drawings, indicates that a number of the particular feature so designated can be included.

FIG. 1 illustrates an example of a system 100 for providing appliances with gas quality information in accordance with one or more embodiments of the present disclosure. As shown in FIG. 1, system 100 includes an area 110 having a plurality of appliances 112-1, 112-2, . . . , 112-N. Area 110 can be, for example, a region such as a plant (e.g., an industrial plant) that may include a number of structures (e.g., buildings).

Appliances 112-1, 112-2, . . . , 112-N can be appliances that utilize fuel (e.g., gas) to perform their operations. For example, appliances 112-1, 112-2, . . . , 112-N can be appliances used in drying or air heating applications, such as, for instance, paper machines, agricultural grain dryers, tissue machines, and food and beverage (e.g., beer) processing machines. However, embodiments of the present disclosure are not limited to a particular type(s) of appliance.

Although not shown in FIG. 1 for clarity and so as not to obscure embodiments of the present disclosure, each appliance 112-1, 112-2, . . . , 112-N may include an air-fuel or oxygen-fuel ratio controller. The air-fuel or oxygen-fuel ratio controller can adjust the air-fuel or oxygen-fuel ratio of the appliance, as will be further described herein.

Further, although not shown in FIG. 1 for clarity and so as not to obscure embodiments of the present disclosure, each appliance 112-1, 112-2, . . . , 112-N may include a user interface. The user interface can provide (e.g., display and/or present) information (e.g., data) to the user of the appliance, and/or receive information (e.g., input) from the user of the appliance. For example, the user interface can be a graphical user interface (GUI) that can include a display (e.g., a screen) that can provide and/or receive information to and/or from the user of the appliance. The display can be, for instance, a touch-screen (e.g., the GUI can include touch-screen capabilities). However, embodiments of the present disclosure are not limited to a particular type(s) of user interface.

As shown in FIG. 1, fuel (e.g., gas) can be supplied (e.g., delivered) from a utility (e.g., utility 116) to area 110 (e.g., to appliances 112-1, 112-2, . . . , 112-N in area 110). For example, in the embodiment illustrated in FIG. 1, the gas supplied from utility 116 is input into area 110 at a single (e.g., one) entry point. The gas input into area 110 at the single entry point can then be supplied to appliances 112-1, 112-2, . . . , 112-N (e.g., via pipes or other supply mechanisms), as illustrated in FIG. 1.

As shown in FIG. 1, system 100 can include a single (e.g., only one) calorimeter 114. calorimeter 114 can be located at or adjacent (e.g., near) the entry point of area 110 where the gas is input into area 110, as illustrated in FIG. 1. As such, calorimeter 114 can determine (e.g., measure) the calorific value of the gas being supplied to area 110.

Although the embodiment illustrated in FIG. 1 includes a single calorimeter located at or adjacent the entry point of area 110, in some embodiments a single gas chromatograph may be located at or adjacent the entry point of area 110 instead of a single calorimeter. In such embodiments, the single gas chromatograph can determine properties of the gas being supplied to area 110, such as, for instance, volume percentages of the various components (e.g., methane, ethane, propane, nitrogen, etc.) of the gas. The calorific value of the gas can then be determined based on the determined properties of the gas. For example, the calorific value of the gas can be determined by multiplying the volume percentages by universally accepted heating values per unit volume (e.g., BTUs/cubic foot or kw/cubic meter).

calorimeter 114 (or the gas chromatograph) can communicate the determined calorific value of the gas to appliances 112-1, 112-2, . . . , 112-N (e.g., to the controller of the appliances). For example, in the embodiment illustrated in FIG. 1, calorimeter 114 (or the gas chromatograph) can directly communicate the determined calorific value of the gas to appliances 112-1, 112-2, . . . , 112-N. That is, in the embodiment illustrated in FIG. 1, calorimeter 114 (or the gas chromatograph) can communicate the determined calorific value of the gas to appliances 112-1, 112-2, . . . , 112-N through a direct connection with appliances 112-1, 112-2, . . . , 112-N (e.g., a connection with no intervening elements present between calorimeter 114 and appliances 112-1, 112-2, . . . , 112-N). The direct connection can be, for example, a direct wired connection (e.g., calorimeter 114 and appliances 112-1, 112-2, . . . , 112-N can be coupled through a direct wired connection), or a direct wireless connection (e.g., calorimeter 114 and appliances 112-1, 112-2, . . . , 112-N can be wirelessly coupled). In embodiments in which the direct connection is a direct wireless connection, calorimeter 114 (or the gas chromatograph) and/or appliances 112-1, 112-2, . . . , 112-N can include a transceiver and/or antenna that can transmit and/or receive wireless (e.g., over-the-air) signals, such as, for instance, radio frequency (RF) signals.

In some embodiments, calorimeter 114 (or the gas chromatograph) can communicate the time the calorific value of the gas is determined to appliances 112-1, 112-2, . . . , 112-N. For example, the communication from calorimeter 114 (or the gas chromatograph) can include a time stamp. Appliances 112-1, 112-2, . . . , 112-N can utilize this time information as will be further described herein.

In some embodiments, calorimeter 114 (or the gas chromatograph) can encrypt (e.g., secure) the communication of the determined calorific value. Encrypting the communication can prevent unauthorized access to and/or modification of the communication.

Appliances 112-1, 112-2, . . . , 112-N can adjust (e.g., increase or decrease) their respective air-fuel or oxygen-fuel ratios based, at least in part, on the determined calorific value of the gas. For instance, appliances 112-1, 112-2, . . . , 112-N can adjust their respective air-fuel or oxygen fuel ratios upon receiving the communication of the determined calorific value from calorimeter 114 (or the gas chromatograph). As an example, appliances 112-1, 112-2, . . . , 112-N may adjust their respective air-fuel or oxygen-fuel ratios if the calorific value of the gas has changed (e.g., if the determined calorific value is different from a previous calorific value of the gas).

Appliances 112-1, 112-2, . . . , 112-N can adjust their respective air-fuel or oxygen-fuel ratios by, for example, adjusting (e.g., increasing or decreasing) their respective air or oxygen flows. The adjustment of the air-fuel or oxygen-fuel ratio (e.g., the adjustment of the air or oxygen flow) of the appliance can be performed, for example, by the air-fuel or oxygen-fuel ratio controller of the appliance.

In embodiments in which calorimeter 114 (or the gas chromatograph) communicates the time the calorific value of the gas is determined to appliances 112-1, 112-2, . . . , 112-N (e.g., embodiments in which the communication includes a time stamp), the appliances may use this information to verify that the calorific value is up to date (e.g., was recently determined by calorimeter 114) before adjusting their respective air-fuel or oxygen-fuel ratios. For example, if this information indicates that the calorific value is not up to date (e.g., due to a delay in communicating the calorific value to the appliances), appliances 112-1, 112-2, . . . , 112-N may not adjust their respective air-fuel or oxygen-fuel ratios based on the calorific value.

In some embodiments, each appliance 112-1, 112-2, . . . , 112-N may be aware of the amount of time needed for the gas to travel (e.g., be transported) from the entry point of area 110 to that respective appliance. In such embodiments, each appliance 112-1, 112-2, . . . , 112-N can delay its adjustment of its respective air-fuel or oxygen-fuel ratio based on this amount of time (e.g., such that the adjustment does not occur until the gas has arrived at the appliance).

In some embodiments, appliances 112-1, 112-2, . . . , 112-N may not adjust their respective air-fuel or oxygen-fuel ratios (e.g., may ignore the determined calorific value) if the determined calorific value of the gas is outside a particular (e.g., expected) range. The appliances may instead adjust their respective air-fuel or oxygen-fuel ratios based on a default calorific value or the last calorific value received from calorimeter 114 (or the gas chromatograph) that was within the range, and/or may provide (e.g., issue and/or display) an indication (e.g., a warning and/or error message) to the user of the appliance (e.g., via the user interface of the appliance) that the determined calorific value of the gas is outside the range.

In some embodiments, appliances 112-1, 112-2, . . . , 112-N can provide an indication to the user of the appliance that an adjustment to its maintenance schedule may be needed, and/or propose an adjustment to its maintenance schedule, based, at least in part, on the determined calorific value of the gas. For example, if the determined calorific value of the gas differs from the calorific value of the gas supplied to the appliance at the time of its last maintenance by more than a particular amount, the appliance can propose a recalibration of the appliance.

In some embodiments, appliances 112-1, 112-2, ..., 112-N can provide an indication to the user of the appliance upon calorimeter 114 (or the gas chromatograph) failing to determine the calorific value of the gas or communicate the calorific value of the gas to the appliance. Further, appliances 112-1, 112-2, ..., 112-N can revert to their standard operation (e.g., their air-fuel or oxygen-fuel ratios prior to receiving the calorific value from calorimeter 114) upon calorimeter 114 (or the gas chromatograph) failing to determine the calorific value of the gas or communicate the calorific value of the gas to the appliance.

In some embodiments, calorimeter 114 (or the gas chromatograph) can periodically (e.g., at a particular time interval) determine the calorific value of the gas being supplied to area 110, and communicate the determined calorific value of the gas to appliances 112-1, 112-2, ..., 112-N after each periodic determination. That is, calorimeter 114 (or the gas chromatograph) can periodically update the (e.g., periodically determine an updated) calorific value of the gas, and communicate the updated calorific value to appliances 112-1, 112-2, ..., 112-N.

Appliances 112-1, 112-2, ..., 112-N may adjust their respective air-fuel or oxygen-fuel ratios based, at least in part, on the updated calorific values of the gas. For example, if the most recently updated calorific value received from calorimeter 114 (or the gas chromatograph) is different than the previous calorific value received from calorimeter 114 (or the gas chromatograph), the appliance may adjust its air-fuel or oxygen-fuel ratio accordingly. However, if the most recently updated calorific value is the same as the previously received calorific value, the appliance may not adjust its air-fuel or oxygen-fuel ratio. Further, appliances 112-1, 112-2, ..., 112-N may be aware of the time interval between the periodic updates. As such, appliances 112-1, 112-2, ..., 112-N may be aware of when they will receive the next updated value from calorimeter 114 (or the gas chromatograph).

Figure 2:
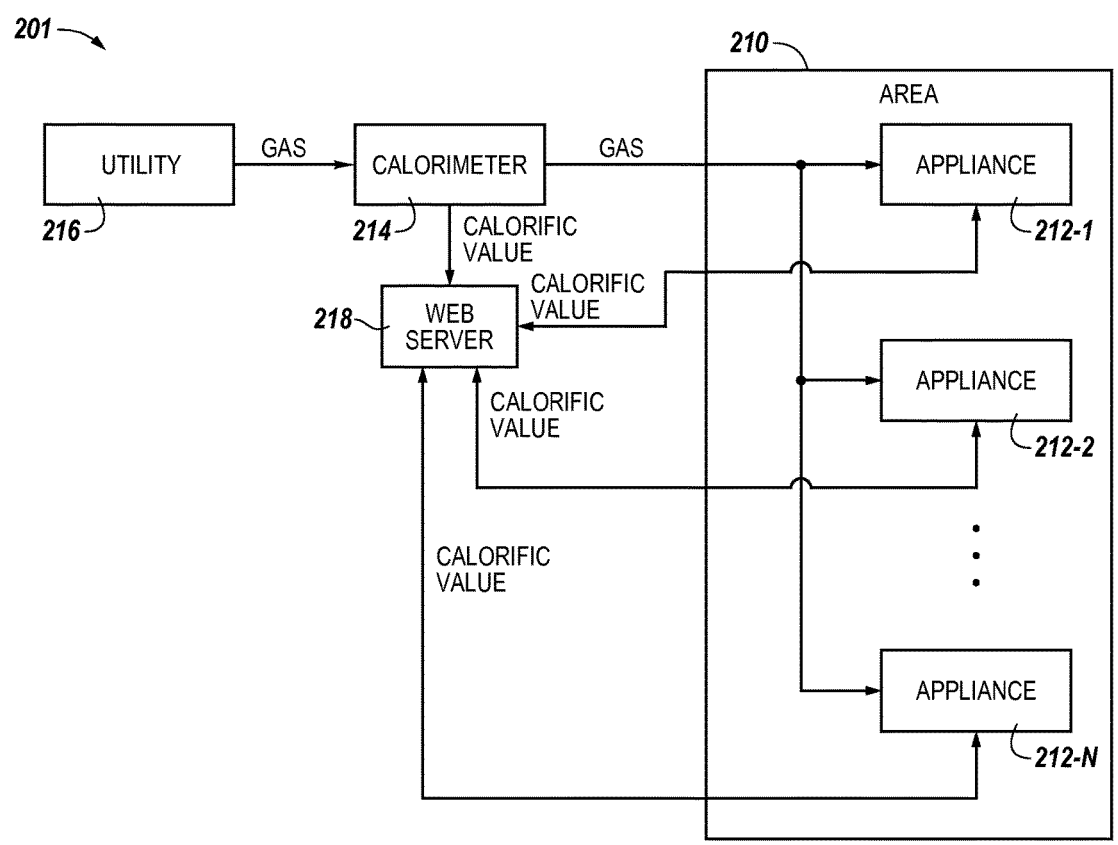
FIG. 2 illustrates an example of a system for providing appliances with gas quality information in accordance with one or more embodiments of the present disclosure.

FIG. 2 illustrates an example of a system 201 for providing appliances with gas quality information in accordance with one or more embodiments of the present disclosure. As shown in FIG. 2, system 201 includes an area 210 having a plurality of appliances 212-1, 212-2, ..., 212-N. Area 210 and appliances 212-1, 212-2, ..., 212-N can be analogous to area 110 and appliances 112-1, 112-2, ..., 112-N, respectively, previously described in connection with FIG. 1. Further, as shown in FIG. 2, fuel (e.g., gas) can be supplied (e.g., delivered) from a utility (e.g., utility 216) to area 210 (e.g., to appliances 212-1, 212-2, ..., 212-N in area 210), in a manner analogous to that previously described in connection with FIG. 1.

As shown in FIG. 2, system 201 can include a single (e.g., only one) calorimeter 214. calorimeter 214 can be located at or adjacent (e.g., near) the entry point of area 210 where the gas is input into area 210, as illustrated in FIG. 2. As such, calorimeter 214 can determine the calorific value of the gas being supplied to area 210, in a manner analogous to calorimeter 114 previously described in connection with FIG. 1. Further, in some embodiments, calorimeter 214 may be replaced by a single gas chromatograph, in a manner analogous to that previously described in connection with FIG. 1.

calorimeter 214 (or the gas chromatograph) can communicate the determined calorific value of the gas to appliances 212-1, 212-2, ..., 212-N (e.g., to the controller of the appliances). For example, in the embodiment illustrated in FIG. 2, system 201 can include a web server 218, and calorimeter 214 (or the gas chromatograph) can communicate the determined calorific value of the gas to appliances 212-2, 212-2, ..., 212-N through web server 218. For instance, calorimeter 214 (or the gas chromatograph) can transmit the calorific value to web server 218, and appliances 212-1, 212-2, ..., 212-N can retrieve the calorific value from web server 218. Further, in some embodiments, calorimeter 214 (or the gas chromatograph) can communicate the time the calorific value of the gas is determined to appliances 212-1, 212-2, ..., 212-N, and/or encrypt the communication of the determined calorific value, in a manner analogous to calorimeter 114 previously described in connection with FIG. 1.

Although not shown in FIG. 2 for clarity and so as not to obscure embodiments of the present disclosure, web server 218 can communicate with calorimeter 214 (or the gas chromatograph) and appliances 212-1, 212-2, ..., 212-N via a network (e.g., via the same network and/or via different networks). For instance, calorimeter 214 (or the gas chromatograph) can transmit the determined calorific value of the gas to web server 218 via a network, and appliances 212-1, 212-2, ..., 212-N can retrieve the calorific value from web server 218 via a network (e.g., via the same network as calorimeter 214, or via a different network).

The network(s) can be a wired or wireless network, such as, for instance, a wide area network (WAN) such as the Internet, a local area network (LAN), a personal area network (PAN), a campus area network (CAN), or metropolitan area network (MAN), among other types of networks. As used herein, a "network" can provide a communication system that directly or indirectly links two or more computers and/or peripheral devices and allows users to access resources on other computing devices and exchange messages with other users. A network can allow users to share resources on their own systems with other network users and to access information on centrally located systems or on systems that are located at remote locations. For example, a network can tie a number of computing devices together to form a distributed control network.

A network may provide connections to the Internet and/or to the networks of other entities (e.g., organizations, institutions, etc.). Users may interact with network-enabled software applications to make a network request, such as to get a file or print on a network printer. Applications may also communicate with network management software, which can interact with network hardware to transmit information between devices on the network.

Appliances 212-1, 212-2, ..., 212-N can adjust their respective air-fuel or oxygen-fuel ratios based, at least in part, on the determined calorific value of the gas, in a manner analogous to appliances 112-1, 112-2, ..., 112-N previously described in connection with FIG. 1. Further, in some embodiments, appliances 212-1, 212-2, ..., 212-N may be aware of the amount of time needed for the gas to travel from the entry point of area 210, may verify that the calorific value is up to date before adjusting their respective air-fuel or oxygen-fuel ratios, may not adjust their respective air-fuel or oxygen-fuel ratios if the calorific value is outside a particular range, may provide an indication to the user of the appliance that an adjustment to its maintenance schedule may be needed, and/or propose an adjustment to its maintenance schedule, based, at least in part, on the determined calorific value of the gas, and/or may provide an indication to the user of the appliance upon calorimeter 214 (or the gas chromatograph) failing to determine the calorific value of the gas or communicate the calorific value of the gas to the appliance, in a manner analogous to appliances 112-1, 112-2, . . . , 112-N.

In some embodiments, calorimeter 214 (or the gas chromatograph) can periodically determine the calorific value of the gas being supplied to area 210, and communicate the determined calorific value of the gas to appliances 212-1, 212-2, . . . , 212-N after each periodic determination, in a manner analogous to calorimeter 114 previously described in connection with FIG. 1. Appliances 212-1, 212-2, . . . , 212-N may adjust their respective air-fuel or oxygen-fuel ratios based, at least in part, on the updated calorific values of the gas, in a manner analogous to appliances 112-1, 112-2, . . . , 112-N previously described in connection with FIG. 1.

Figure 3:
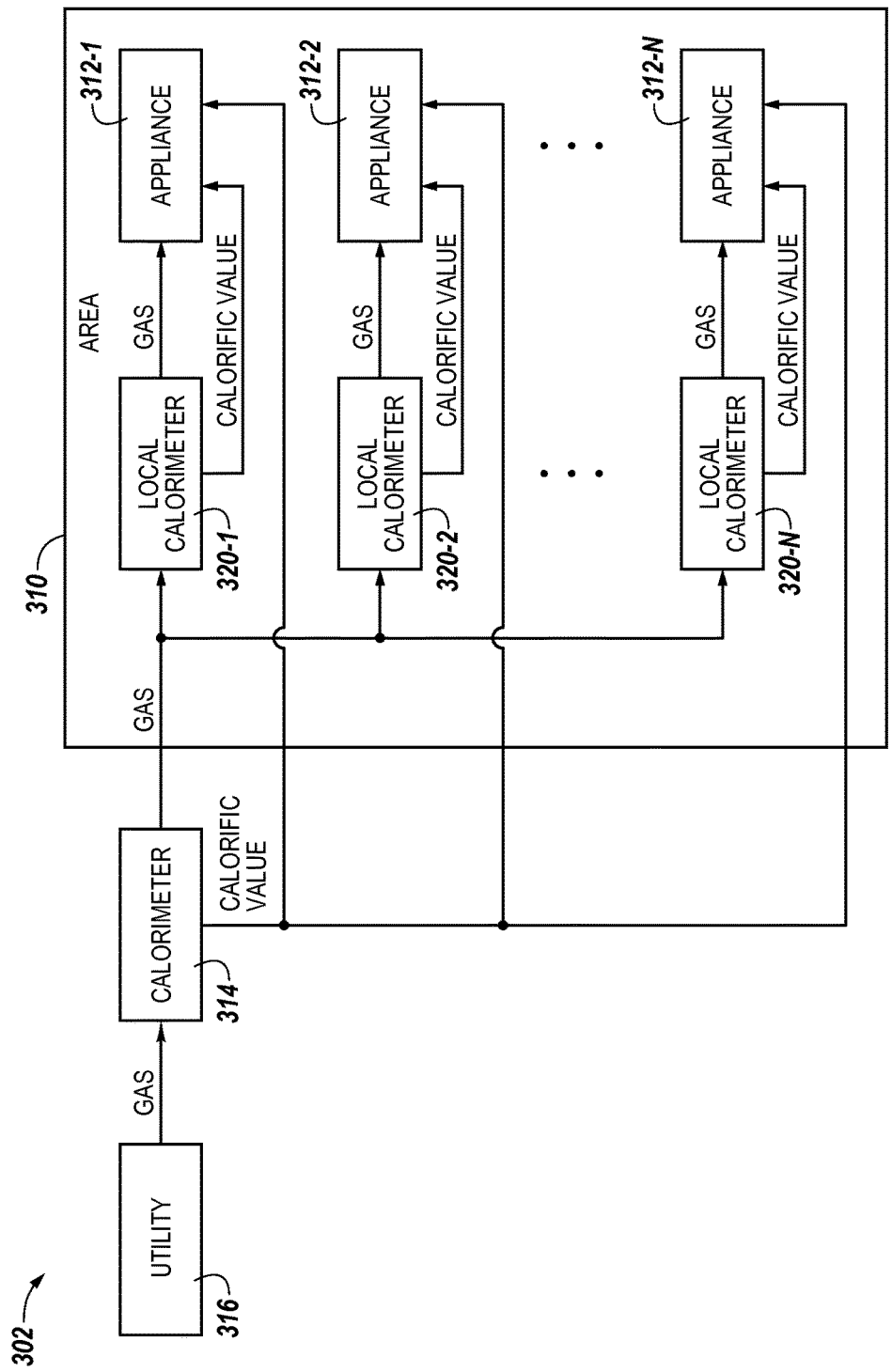
FIG. 3 illustrates an example of a system for providing appliances with gas quality information in accordance with one or more embodiments of the present disclosure.

FIG. 3 illustrates an example of a system 302 for providing appliances with gas quality information in accordance with one or more embodiments of the present disclosure. As shown in FIG. 3, system 301 includes an area 310 having a plurality of appliances 312-1, 312-2, . . . , 312-N. Area 310 and appliances 312-1, 312-2, . . . , 312-N can be analogous to area 110 and appliances 112-1, 112-2, . . . , 112-N, respectively, previously described in connection with FIG. 1. Further, as shown in FIG. 3, fuel (e.g., gas) can be supplied (e.g., delivered) from a utility (e.g., utility 316) to area 310 (e.g., to appliances 312-1, 312-2, . . . , 312-N in area 310), in a manner analogous to that previously described in connection with FIG. 1.

As shown in FIG. 3, system 302 can include a calorimeter 314 located at or adjacent (e.g., near) the entry point of area 310 where the gas is input into area 310, as illustrated in FIG. 3. As such, calorimeter 314 can determine the calorific value of the gas being supplied to area 310, in a manner analogous to calorimeter 114 previously described in connection with FIG. 1. Further, in some embodiments, calorimeter 314 may be replaced by a gas chromatograph, in a manner analogous to that previously described in connection with FIG. 1.

calorimeter 314 (or the gas chromatograph) can communicate the determined calorific value of the gas to appliances 312-1, 312-2, . . . , 312-N (e.g., to the controller of the appliances). For example, in the embodiment illustrated in FIG. 3, calorimeter 314 (or the gas chromatograph) can directly communicate the determined calorific value of the gas to appliances 312-1, 312-2, . . . , 312-N in a manner analogous to that previously described in connection with FIG. 1. However, embodiments of the present disclosure are not so limited. For example, in some embodiments, calorimeter 314 (or the gas chromatograph) can communicate the determined calorific value of the gas to appliances 312-2, 312-2, . . . , 312-N through a web server, in a manner analogous to that previously described in connection with FIG. 2. Further, in some embodiments, calorimeter 314 (or the gas chromatograph) can communicate the time the calorific value of the gas is determined to appliances 312-1, 312-2, . . . , 312-N, and/or encrypt the communication of the determined calorific value, in a manner analogous to calorimeter 114 previously described in connection with FIG. 1.

Appliances 312-1, 312-2, . . . , 312-N can adjust their respective air-fuel or oxygen-fuel ratios based, at least in part, on the determined calorific value of the gas, in a manner analogous to appliances 112-1, 112-2, . . . , 112-N previously described in connection with FIG. 1.

Further, in some embodiments, appliances 312-1, 312-2, . . . , 312-N may be aware of the amount of time needed for the gas to travel from the entry point of area 310, may verify that the calorific value is up to date before adjusting their respective air-fuel or oxygen-fuel ratios, may not adjust their respective air-fuel or oxygen-fuel ratios if the calorific value is outside a particular range, may provide an indication to the user of the appliance that an adjustment to its maintenance schedule may be needed, and/or propose an adjustment to its maintenance schedule, based, at least in part, on the determined calorific value of the gas, and/or may provide an indication to the user of the appliance upon calorimeter 314 (or the gas chromatograph) failing to determine the calorific value of the gas or communicate the calorific value of the gas to the appliance, in a manner analogous to appliances 112-1, 112-2, . . . , 112-N.

In some embodiments, calorimeter 314 (or the gas chromatograph) can periodically determine the calorific value of the gas being supplied to area 310, and communicate the determined calorific value of the gas to appliances 312-1, 312-2, . . . , 312-N after each periodic determination, in a manner analogous to calorimeter 114 previously described in connection with FIG. 1. Appliances 312-1, 312-2, . . . , 312-N may adjust their respective air-fuel or oxygen-fuel ratios based, at least in part, on the updated calorific values of the gas, in a manner analogous to appliances 112-1, 112-2, . . . , 112-N previously described in connection with FIG. 1.

As shown in FIG. 3, system 302 can include a plurality of additional (e.g., local) calorimeters 320-1, 320-2, . . . , 320-N in area 310. Each local calorimeter 320-1, 320-2, . . . , 320-N can be located at or adjacent (e.g., near) the entry point of a different one of appliances 312-1, 312-2, . . . , 312-N where gas is input into the appliance, as illustrated in FIG. 3. That is, calorimeter 320-1 can be located at or adjacent the entry point of appliance 312-1 where gas is input into appliance 312-1, calorimeter 320-1 can be located at or adjacent the entry point of appliance 312-2 where gas is input into appliance 312-2, etc., as illustrated in FIG. 3. As such, each calorimeter 320-1, 320-2, . . . , 320-N can determine the calorific value of the gas being supplied to its respective appliance. That is, calorimeter 320-1 can determine the calorific value of the gas being supplied to appliance 312-1, calorimeter 320-2 can determine the calorific value of the gas being supplied to appliance 312-2, etc. As an additional example, in some embodiments, one local calorimeter may be shared among a plurality of appliances.

Each calorimeter 320-1, 320-2, . . . , 320-N can communicate its determined calorific value to its respective appliance (e.g., to the controller of the appliance). That is, calorimeter 320-1 can communicate its determined calorific value to appliance 312-1, calorimeter 320-2 can communicate its determined calorific value to appliance 312-2, etc. In the embodiment illustrated in FIG. 3, each calorimeter 320-1, 320-2, . . . , 320-N can directly (e.g., through a direct wired connection) communicate its determined calorific value to its respective appliance.

Appliances 312-1, 312-2, . . . , 312-N can adjust their respective air-fuel or oxygen-fuel ratios based, at least in part, on the calorific value communicated from its respective local calorimeter. For example, appliances 312-1, 312-2, . . . , 312-N can adjust their respective air-fuel or oxygen-fuel ratios based on both the calorific value communicated from its respective local calorimeter and the calorific value communicated from calorimeter 314 (or the gas chromatograph). That is, appliance 312-1 can adjust its air-fuel or oxygen-fuel ratio based on the calorific value communicated from calorimeter 320-1 and the calorific value communicated from calorimeter 314 (or the gas chromatograph), appliance 312-2 can adjust its air-fuel or oxygen-fuel ratio based on the calorific value communicated from calorimeter 320-2 and the calorific value communicated from calorimeter 314 (or the gas chromatograph), etc.

As an example, each appliance 312-1, 312-2, ..., 312-N can calibrate the calorific value communicated from its respective local calorimeter based on the calorific value communicated from calorimeter 314 (or the gas chromatograph). For instance, each appliance 312-1, 312-2, ..., 312-N can compare the calorific value communicated from its respective local calorimeter to the calorific value communicated from calorimeter 314 (or the gas chromatograph), and adjust the calorific value communicated from its respective local calorimeter to account for any difference between the two calorific values. The appliance can then adjust its air-fuel or oxygen-fuel ratio based on the calibrated (e.g., adjusted) calorific value. This can improve the accuracy of local calorimeters 320-1, 320-2, ..., 320-N.

In some embodiments, each calorimeter 320-1, 320-2, ..., 320-N can determine the calorific value of the gas being supplied to its respective appliance, and communicate its determined calorific value to its respective appliance, upon a failure of calorimeter 314 (or the gas chromatograph) (e.g., upon calorimeter 314 failing to determine the calorific value of the gas being supplied to area 310 and/or communicate the calorific value to appliances 312-1, 312-2, ..., 312-N). In such embodiments, local calorimeters 320-1, 320-2, ..., 320-N can act as backups for calorimeter 314 (or the gas chromatograph) when calorimeter 314 (or the gas chromatograph) is not working.

In some embodiments, each calorimeter 320-1, 320-2, ..., 320-N can determine the calorific value of the gas being supplied to its respective appliance, and communicate its determined calorific value to its respective appliance, more frequently than calorimeter 314 (or the gas chromatograph) determines the calorific value of the gas being supplied to area 310 and communicates the determined value to appliances 312-1, 312-2, ..., 312-N. Such embodiments could reduce the frequency at which appliances 312-1, 312-2, ..., 312-N would have to receive communications from calorimeter 314 (or the gas chromatograph).

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A system for providing appliances with gas quality information, comprising:
    a single calorimeter configured to:
        determine a calorific value of a gas being supplied to an area having a plurality of appliances;
        directly communicate the calorific value of the gas to the plurality of appliances; and
        communicate a time when the calorific value of the gas is determined to the plurality of appliances, the plurality of appliances are configured to use the time when the calorific value of the gas is determined to verify that the calorific value of the gas is up to date before adjusting their respective air-fuel or oxygen-fuel ratios;
    wherein the plurality of appliances are configured to adjust their respective air-fuel or oxygen-fuel ratios if the calorific value of the gas is different from a previous calorific value of the gas being supplied to the area.

2. The system of claim 1, wherein the single calorimeter is located at or adjacent an entry point of the area.

3. The system of claim 1, wherein the single calorimeter is configured to communicate the calorific value of the gas to the plurality of appliances through a web server.

4. The system of claim 1, wherein the single calorimeter is configured to:
    periodically determine the calorific value of the gas; and
    communicate the calorific value of the gas to the plurality of appliances after each periodic determination.

5. The system of claim 1, wherein the single calorimeter is configured to communicate a time the calorific value of the gas is determined to the plurality of appliances.

6. A method for providing appliances with gas quality information, comprising:
    determining, by a single calorimeter at a point where gas is input into an area, a calorific value of the gas;
    directly communicating the calorific value of the gas from the single calorimeter to a plurality of appliances in the area;
    communicating a time when the calorific value of the gas is determined to the plurality of appliances, the plurality of appliances are configured to use the time when the calorific value of the gas is determined to verify that the calorific value of the gas is up to date before adjusting their respective air-fuel or oxygen-fuel ratios; and
    adjusting, by the plurality of appliances, their respective air-fuel or oxygen-fuel ratios if the calorific value of the gas is different from a previous calorific value of the gas being input into the area.

7. The method of claim 6, wherein the method includes communicating the calorific value of the gas from the single calorimeter to the plurality of appliances through a direct wired connection.

8. The method of claim 6, wherein the method includes communicating the calorific value of the gas from the single calorimeter to the plurality of appliances through a direct wireless connection.

9. The method of claim 6, wherein the method includes encrypting the communication of the calorific value of the gas from the single calorimeter to the plurality of appliances.

10. The method of claim 6, wherein the method includes providing an indication to a user of the plurality of appliances upon the single calorimeter failing to determine the calorific value of the gas or communicate the calorific value of the gas to the plurality of appliances.

11. A system for providing appliances with gas quality information, comprising:
an area having a plurality of appliances; and
a calorimeter located at or adjacent an entry point of the area, wherein the calorimeter is configured to:
determine a calorific value of a gas being supplied to the area;
directly communicate the calorific value of the gas to the plurality of appliances; and
communicate a time when the calorific value of the gas is determined to the plurality of appliances, the plurality of appliances are configured to use the time when the calorific value of the gas is determined to verify that the calorific value of the gas is up to date before adjusting their respective air-fuel or oxygen-fuel ratios; and
wherein the plurality of appliances are configured to adjust their respective air-fuel or oxygen-fuel ratios if the calorific value of the gas is different from a previous calorific value of the gas being supplied to the area.

12. The system of claim 11, wherein the system includes a plurality of additional calorimeters, wherein:
each additional calorimeter is located at or adjacent an entry point of a different one of the plurality of appliances; and
each additional calorimeter is configured to:
determine a calorific value of a gas being supplied to its respective appliance; and
communicate its determined calorific value to its respective appliance.

13. The system of claim 12, wherein each appliance is configured to:
calibrate the calorific value communicated from its respective additional calorimeter based on the calorific value communicated from the calorimeter located at or adjacent the entry point of the area; and
adjust its air-fuel or oxygen-fuel ratio based, at least in part, on the calibrated calorific value.

14. The system of claim 12, wherein each additional calorimeter is configured to determine the calorific value of the gas being supplied to its respective appliance and communicate its determined calorific value to its respective appliance upon the calorimeter located at or adjacent the entry point of the area failing to determine the calorific value of the gas being supplied to the area or communicate the calorific value of the gas to the plurality of appliances.

15. The system of claim 12, wherein each additional calorimeter is configured to determine the calorific value of the gas being supplied to its respective appliance and communicate its determined calorific value to its respective appliance more frequently than the calorimeter located at or adjacent the entry point of the area is configured to determine the calorific value of the gas being supplied to the area and communicate the calorific value of the gas to the plurality of appliances.

16. The system of claim 11, wherein:
each appliance is aware of an amount of time needed for the gas to travel from the entry point to that respective appliance; and
each appliance is configured to delay its adjustment of its respective air-fuel or oxygen-fuel ratio based on the amount of time.

17. The system of claim 11, wherein the plurality of appliances are configured to not adjust their respective air-fuel or oxygen-fuel ratios if the calorific value of the gas is outside a particular range.

18. The system of claim 11, wherein the plurality of appliances are configured to propose an adjustment to their respective maintenance schedules based, at least in part, on the calorific value of the gas.

* * * * *